(12) United States Patent
Ursella

(10) Patent No.: US 11,525,789 B2
(45) Date of Patent: Dec. 13, 2022

(54) APPARATUS AND METHOD FOR PERFORMING A COMPUTED TOMOGRAPHY SCAN OF AN OBJECT WHICH HAS AN ELONGATE SHAPE, IN PARTICULAR WOODEN BOARDS

(71) Applicant: MICROTEC S.R.L., Bressanone (IT)

(72) Inventor: Enrico Ursella, Mestre (IT)

(73) Assignee: MICROTEC S.R.L., Bressanone (IT)

( * ) Notice: Subject to any disclaimer, the term of this patent is extended or adjusted under 35 U.S.C. 154(b) by 146 days.

(21) Appl. No.: 17/176,017

(22) Filed: Feb. 15, 2021

(65) Prior Publication Data

US 2021/0270756 A1    Sep. 2, 2021

(30) Foreign Application Priority Data

Feb. 28, 2020   (IT) ........................ 102020000004246

(51) Int. Cl.
*G01N 23/04*   (2018.01)
*G06T 7/00*   (2017.01)
(Continued)

(52) U.S. Cl.
CPC ......... *G01N 23/046* (2013.01); *G06T 7/0004* (2013.01); *G01N 33/46* (2013.01);
(Continued)

(58) Field of Classification Search
CPC .............. G01N 23/046; G01N 33/46; G01N 2223/619; G01N 2223/631; G06T 7/0004; G06T 2207/30108; G06T 2211/40
See application file for complete search history.

(56) References Cited

U.S. PATENT DOCUMENTS 11,120,540 B2 *  9/2021  Mairhofer ............ H04N 5/2256
2002/0168083 A1  11/2002  Garms et al.
(Continued)

FOREIGN PATENT DOCUMENTS

EP    3220143 A1    9/2017
EP    3690429 A1    8/2020
(Continued)

OTHER PUBLICATIONS

Beister, Marcel, et al, "Iterative Reconstruction Methods in X-ray CT", Physica Medica, vol. 28 (2012) pp. 94-108.
(Continued)

*Primary Examiner* — Mark R Gaworecki
(74) *Attorney, Agent, or Firm* — Pearne & Gordon LLP

(57) ABSTRACT

Apparatus and method for performing computed tomography scans of elongate objects, wherein the object is irradiated with X-rays emitted by a plurality of X-ray emitters which are offset relative to a forward movement direction transversal to the main axis of the object, wherein a rotation device rotates each object about its own main axis of extension while the object is irradiated by one or more beams of X-rays, wherein electronic identifying means estimate the instantaneous position and orientation of the axial portions of the object which are irradiated during the rotation, and wherein an electronic processing and control unit is programmed for combining sets of radiographic data acquired for each axial portion of the object at different detecting moments during the rotation, for processing a three-dimensional tomography reconstruction of the object while taking into account corresponding information about the position and the orientation of each axial portion at each moment.

27 Claims, 6 Drawing Sheets

(51) Int. Cl.
*G01N 23/046* (2018.01)
*G01N 33/46* (2006.01)

(52) U.S. Cl.
CPC . *G01N 2223/619* (2013.01); *G01N 2223/631* (2013.01); *G06T 2207/30108* (2013.01); *G06T 2211/40* (2013.01)

(56) References Cited

U.S. PATENT DOCUMENTS

| | | |
|---|---|---|
| 2004/0057551 A1 | 3/2004 | Skatter et al. |
| 2017/0270657 A1 | 9/2017 | Eisner et al. |
| 2020/0184620 A1* | 6/2020 | Biernacki ............. G06T 7/0004 |
| 2020/0375203 A1* | 12/2020 | Pfanstiel ............. G01N 23/083 |
| 2021/0163231 A1* | 6/2021 | Connelly ............... B65G 43/08 |

FOREIGN PATENT DOCUMENTS

| | | |
|---|---|---|
| WO | 02/091286 A2 | 11/2002 |
| WO | 02/091286 A3 | 11/2002 |
| WO | WO-2019081875 A1 * | 5/2019 ............. B07C 5/122 |

OTHER PUBLICATIONS

Jin, Kyong Hwan, et al., "Deep Convolutional Neural Network for Inverse Problems in Imaging", IEEE Transactions On Image Processing, vol. 26, No. 9, Sep. 2017, p. 4509-4522.
Ursella, Enrico et al, Italian Patent Application No. 102019000019454 filed Oct. 21, 2019 and English translation thereof, total 72 pages.

* cited by examiner

APPARATUS AND METHOD FOR PERFORMING A COMPUTED TOMOGRAPHY SCAN OF AN OBJECT WHICH HAS AN ELONGATE SHAPE, IN PARTICULAR WOODEN BOARDS

This invention relates to an apparatus and a method for performing a computed tomography scan of an object which has an elongate shape along a main axis of extension, in particular of objects of relatively large size, such as the wooden boards commonly processed in sawmills.

In the context of this invention the term tomography inspection means the reconstruction of a three-dimensional model constituted of a plurality of voxels, and which is correlated with the density of the object. In particular, associated with each voxel there may be either values correlated with the absolute density of the object in that zone, or values correlated with the variation of density in that zone (such as values representative of the density gradient). In the context of this description and of the appended claims, the definition of a three-dimensional model obtained with a tomography inspection also includes models which present more or less large approximations relative to the real values; what matters is that the model is suitable for the type of information to be obtained (for example, for detecting the presence or absence of solid foreign bodies in an object a very approximate assessment of the local density variation may even be sufficient).

This invention was initially defined with reference to processing wooden boards in wood processing plants. Therefore, reference will mainly be made to that type of application hereinafter. In spite of that, it shall be understood that this invention may also be applicable to any other object having an elongate shape, such as products made of plastic, metal or composite materials; for example it may be applied for section bars, moulded items or cast products but also to pieces made or assembled having a large size which often need to be checked.

As is known, tomography is a non-destructive evaluation technique, which may be used both for sample evaluations and in an industrial production line for systematic analysis of pieces produced.

However, the latter use is not very widespread in industry, since almost all existing tomography scanners are too slow, and in any case allow a low number of scans per hour, approximately several units per hour.

The most high-performance solutions currently on the market include those defined by the Applicant which are capable of performing tomography scans in an industrial environment and which allow working with objects which are moved forward on a conveyor with speeds of between 40 m/min and 180 m/min. They are apparatuses which comprise a rotary gantry, which rotates about the forward movement direction of the objects to be inspected, and wherein the combined motion of the objects and of the gantry causes helical irradiating of the object.

However, in the case of objects having an elongate shape, this linear speed is not sufficient to guarantee the productivity required by modern industrial plants.

For example, in wooden board processing plants, a processing speed of 40 boards/min is quite common, but even 100 boards/min is often reached. Considering that the typical length of a board is 6 metres, and taking into account a gap, however small, between two successive boards, this productivity corresponds to a speed of the boards on the longitudinal conveyor of between 300 m/min and 1000 m/min.

Making a tomography scanner which allows a tomography scan to be performed at these speeds would be very complicated and expensive.

It should also be noticed that similar problems also arise for all of the other measurements and checks which must be performed on the boards (such as scans based on colour video cameras, scatter lasers and X-rays). For such measuring systems, industrial solutions are increasingly leaning towards solutions wherein the measurement is performed during the transversal conveying of the boards. Indeed, since the typical width of a wooden board is 30 cm, in this way it is possible to measure for example 100 boards/min with a forward movement speed of around 60 m/min, much lower than the 1000 m/min which would in contrast be required in the case of longitudinal forward movement.

As regards the advantages of a tomography evaluation of the wooden boards over all other evaluation methods used, the main advantage is the possibility of assessing the following characteristics (most of which are not measurable with common inspection techniques based on observation from the outside or performing simple X-rays):

the position of the pith inside the board;
the shape of the knot inside the board, in particular for calculating the "Knot displacement" index often used in North American standards for assessment of the quality of wood;
the size of sound knots;
the presence of internal crevices or in any case those not perpendicular to the surface;
the presence of surface or internal resin pockets;
the trend of the direction of the fibre.

In case of applications in other sectors, the tomography inspection may be used for checking the quality of products having an elongate shape which are made of plastic, metal or composite materials, such as section bars, moulded items or cast products but also pieces made or assembled having a large size. The results of the tomography evaluations may be used either for rejecting non-conforming pieces or for issuing commands for successive processing operations.

Although having available a tomography scanner capable of inspecting elongate objects, and in particular wooden boards, as they are moved forward positioned transversally relative to the forward movement direction may seem absolutely desirable, accomplishing this means facing technical obstacles which are apparently insurmountable, at least at acceptable costs for industrial applications.

As far as the Applicant is aware, for example, the maximum scanning diameter of a tomography scanner currently on the market is approximately 1 metre, and making one with a 6 metre capacity (that is to say, capable of accommodating boards of typical length) appears to be technically highly complex (with the need to use giant sensors and to rotate very significant weights with equally high tangential speeds) and economically unsustainable (without considering the dimensions that such a tomography scanner would have inside the plant).

In this context the technical purpose which forms the basis of this invention is to provide an apparatus and a method for performing a computed tomography scan of objects which have an elongate shape, which overcomes the above-mentioned disadvantages.

In particular the technical purpose of this invention is to provide an apparatus and a method for performing a computed tomography scan of objects which have an elongate shape, whose cost is comparable to that of the apparatuses currently known but which allow the productivity required by the market even for objects having large dimensions such as wooden boards.

The technical purpose specified and the aims indicated are substantially achieved by an apparatus and a method for performing a computed tomography scan of objects which have an elongate shape, as described in the appended claims.

Further features and the advantages of this invention are more apparent in the detailed description, with reference to the accompanying drawings which illustrate several preferred, non-limiting embodiments of an apparatus and a method for performing a computed tomography scan of objects which have an elongate shape, in which.

Figure 1:
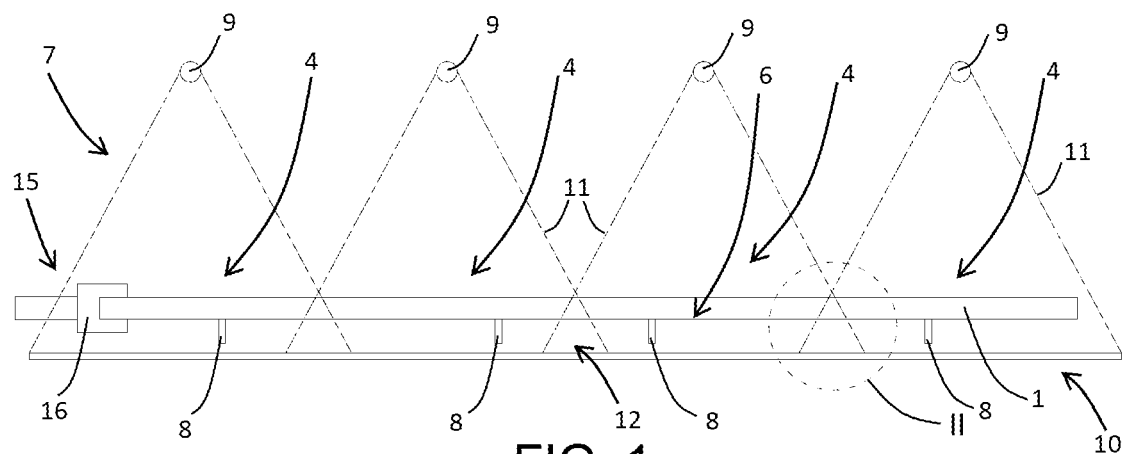
FIG. 1 is a schematic front view of a scanning zone of an apparatus according to a first embodiment of this invention.

The following is initially a description of several preferred embodiments of the apparatus according to this invention and then the method according to this invention. It should be noticed that the method according to this invention may be implemented either by means of the apparatus described and claimed, or with other apparatuses suitable for the purpose.

In any case, what is described with reference, respectively, to the apparatus and to the method, shall be understood to also apply respectively for the method and for the apparatus if technically possible.

The inventive idea forming the basis of this invention was that of performing the tomography scan of elongate objects 1 while moving them forward along a forward movement direction 2 so that they are positioned with their main axis of extension 3 transversal (preferably perpendicular) to the forward movement direction 2 itself, rotating the objects 1 about their own main axis of extension 3 rather than about an axis parallel to the forward movement direction 2, and performing the tomography scan using a stationary radiographic system, positioned transversally to the forward movement direction 2. Moreover, since the objects 1 are long, advantageously multiple X-ray sources are used, each of which irradiates only one portion of the object 1; that portion of object 1, hereinafter defined as the "axial portion 4" is identifiable as a sort of slice of the object 1, which comprises the whole width and the whole thickness of the object 1, but which only extends along part of the main axis of extension 3. Therefore, in the context of this description, the "axial portion 4" defined in this way must not be understood as a part of the object 1 separate from the rest, but as a simple subset of its volume which extends between two positions along the main axis of extension 3 and which is affected by a single beam 11 of X-rays.

Therefore, along the main axis of extension 3 of each object 1 a plurality of axial portions 4 of the object 1 may be identifiable, which may even partly overlap each other.

The apparatus according to this invention comprises first a conveyor 5 configured for conveying along a forward movement direction 2, objects 1 which are positioned on a forward movement plane 6 with their main axis of extension 3 transversal to the forward movement direction 2. Similarly to what happens in all prior art tomography scanners equipped with a conveyor 5, the conveyor 5 according to this invention is configured for conveying the objects 1 from an infeed zone to an outfeed zone (which are not illustrated) by making them pass through at least one scanning zone 7. The forward movement plane 6 is parallel both to the forward movement direction 2 and to the main axis of extension 3 of the objects 1 and, preferably, is horizontal.

In the preferred embodiment illustrated in the accompanying figures, the conveyor 5 is a conveyor 5 with chains 8 arranged side by side.

In the known way, at least the scanning zone 7, but preferably also the entire conveyor 5, will then be surrounded by special X-ray screens (which are not illustrated), suitable for as far as possible limiting the escape of X-rays from the scanning zone 7, towards the surrounding environment.

At the scanning zone 7, the apparatus comprises a plurality of X-ray emitters 9 and an X-ray detecting device 10 which are facing each other and the conveyor 5. The X-ray emitters 9 and the X-ray detecting device 10 are stationary relative to the conveyor 5 and are positioned on opposite sides of the forward movement plane 6 defined by it, that is to say, the X-ray emitters 9 are located, respectively, either above or below the forward movement plane 6 and the X-ray detecting device 10 is consequently located, respectively, either below or above that plane. Moreover, the beams of X-rays are emitted with a central axis transversal to the forward movement plane 6 and preferably perpendicular to it.

An electronic processing and control unit (not illustrated) is programmed for processing a three-dimensional tomography reconstruction of the object 1 using the readings of the detecting device 10, similarly to what happens in all computed tomography scanners, but in the specific ways described below.

The function of the X-ray emitters 9 is in use to emit respective beams 11 of X-rays towards each object 1 which passes through the scanning zone 7. Advantageously each X-ray emitter 9 emits a beam 11 of X-rays, preferably of the divergent type (that is to say, of the "cone beam" type). Moreover preferably each beam 11 of X-rays is emitted with a substantially rectangular cross-section.

Each beam 11 of X-rays, perpendicularly to its own central axis, has a longitudinal dimension (that is to say, parallel to the forward movement direction 2) large enough to affect the whole width of the object 1 during its entire rotation about the main axis of extension 3, and a transversal dimension (perpendicular to the forward movement direction 2) less than the width of the conveyor 5 (as well as less than the maximum length allowed for the objects 1 to be inspected). Therefore, each beam 11 of X-rays has a size sufficient to cover an axial portion 4 of the object 1 for all of the time necessary to obtain the radiographic data necessary for the tomography reconstruction, according to the ways described below.

In order to guarantee that the object 1 is subjected to the tomography inspection along all of its main axial extent, the beams 11 of X-rays emitted by the X-ray emitters 9 are offset from each other with reference to the forward movement direction 2. In particular, the beam 11 of X-rays emitted by each X-ray emitter 9 is offset relative to the beams 11 of X-rays emitted by the other X-ray emitters 9, in such a way that each beam 11 of X-rays irradiates an axial portion 4 of each object 1 which is at least partly distinct from the axial portions 4 irradiated by the other beams 11 of X-rays. In other words, the beams 11 of X-rays are positioned in such a way that the projections on a straight line perpendicular to the forward movement direction 2, of their intersections with the forward movement plane 6, are at least partly offset and, preferably, cover the whole width of the conveyor 5.

Figure 5:
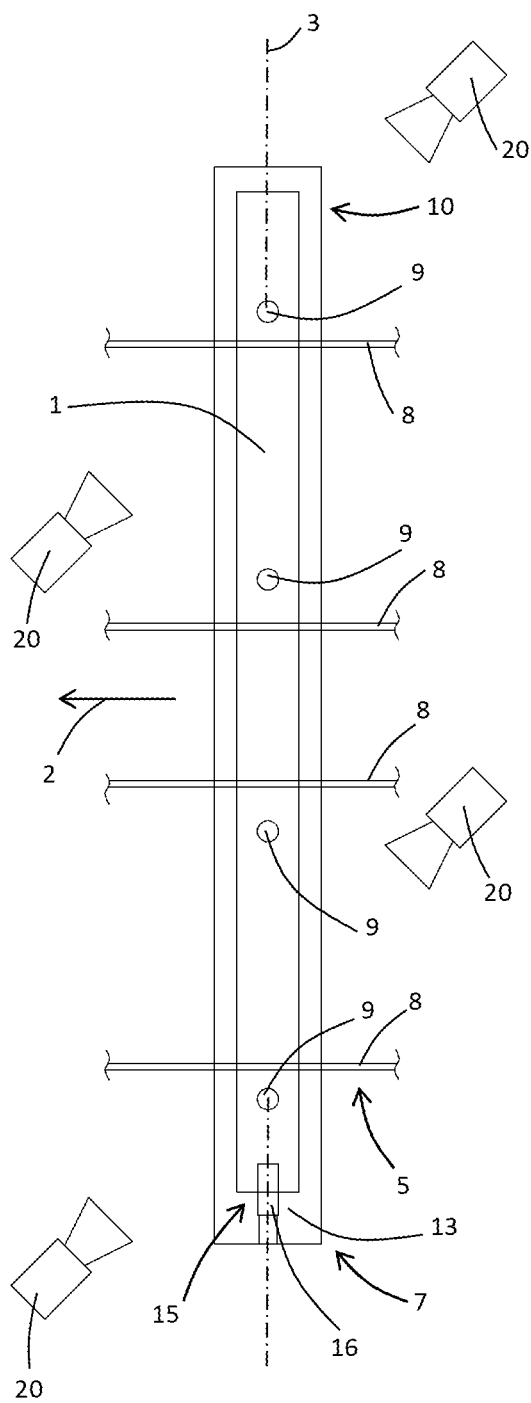
FIG. 5 is a schematic top view of the scanning zone of FIG. 1, showing some parts which are not visible in FIG. 1.
Figure 6:
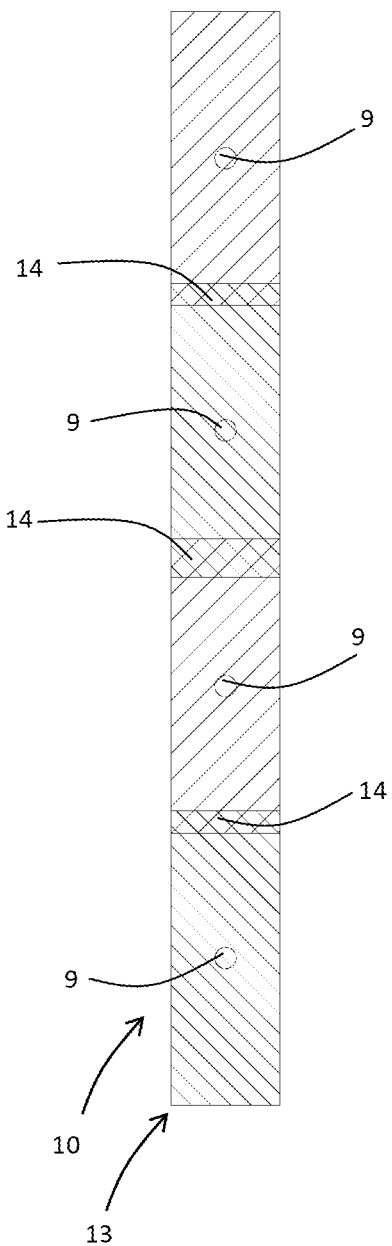
FIG. 6 is a schematic top view showing the incidence of different beams of X-rays on a detecting device of the apparatus of FIG. 5.
Figure 7:
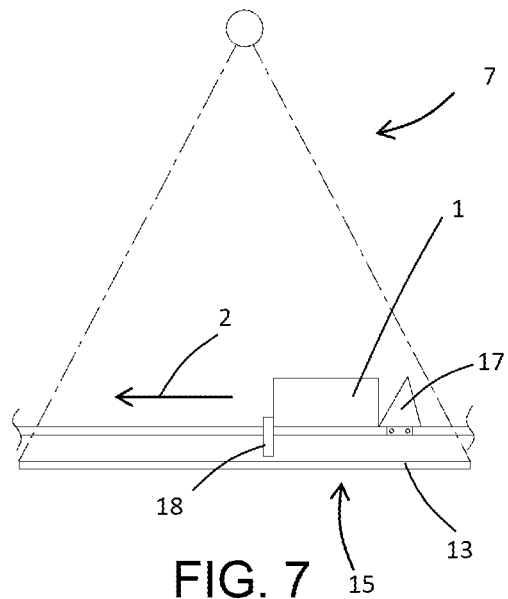
FIG. 7 is a schematic side view of a scanning zone of an apparatus according to a second embodiment of this invention, in a first operating configuration.
Figure 8:
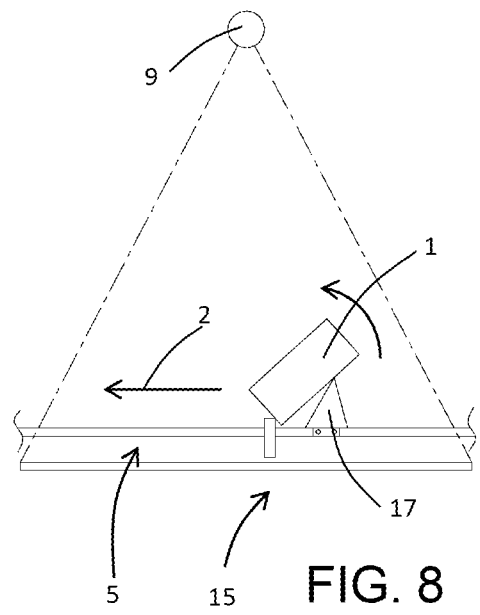
FIGS. 8 to 11 show the scanning zone of FIG. 7 during a sequence of operating configurations which cause a board to overturn relative to the starting position illustrated in FIG. 7.
Figure 9:
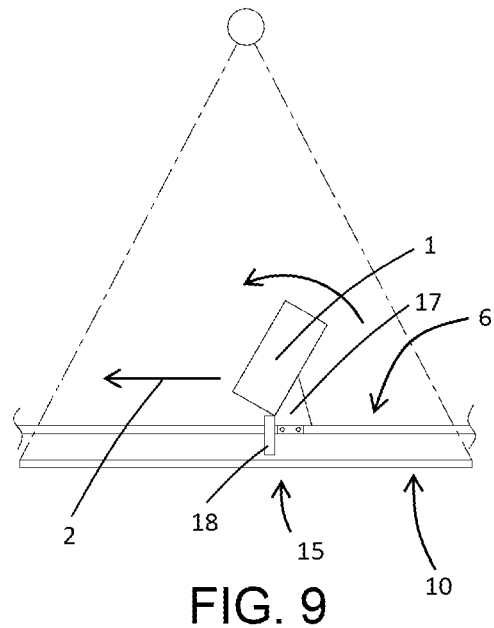
Figure 10:
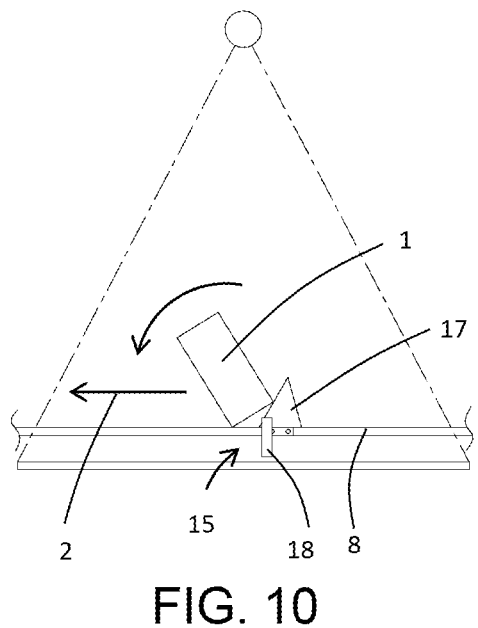
Figure 11:
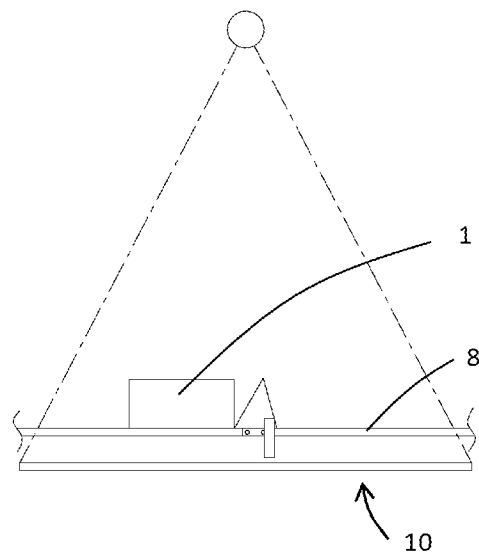
Figure 12:
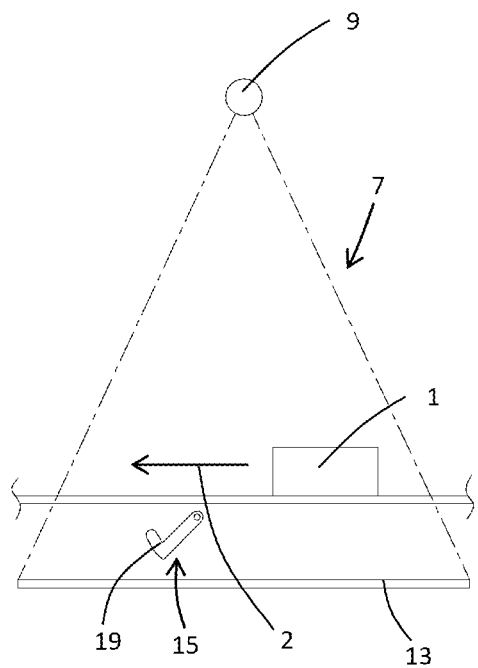
FIG. 12 is a schematic side view of a scanning zone of an apparatus according to a third embodiment of this invention in a first operating configuration.
Figure 13:
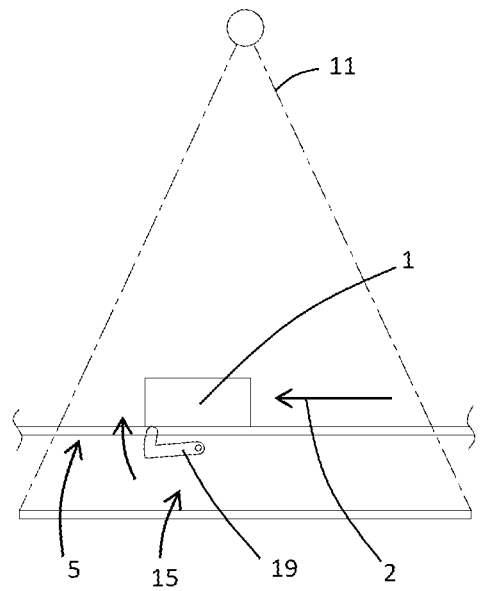
FIGS. 13 to 16 shows the scanning zone of FIG. 12 during a sequence of operating configurations which cause a board to overturn relative to the starting position illustrated in FIG. 12.
Figure 14:
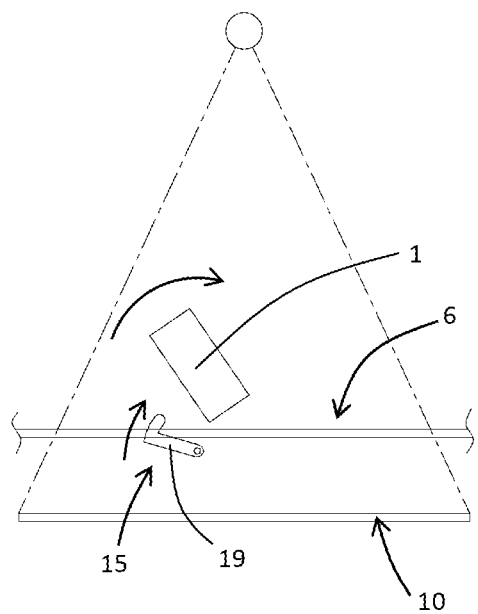
Figure 15:
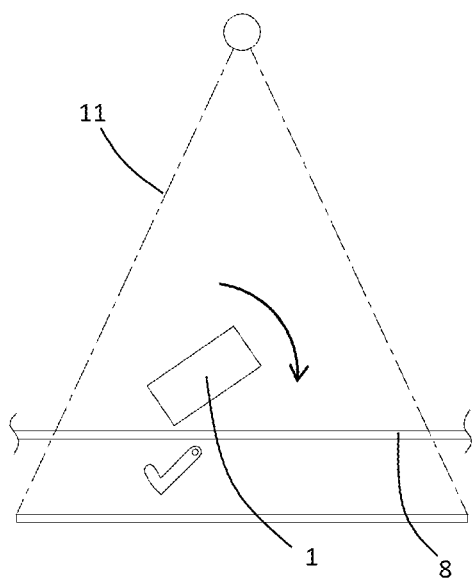
Figure 16:
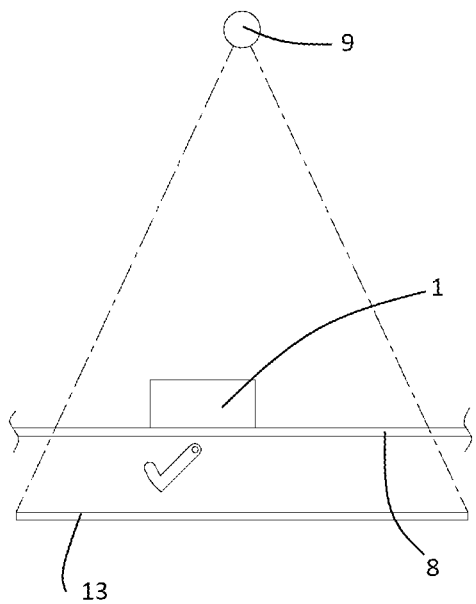

According to a first preferred embodiment, the X-ray emitters 9 are grouped in a single group and are configured in such a way as to emit respective beams 11 of X-rays which are side by side, one after another, in a direction transversal to the forward movement direction 2. That result may advantageously be obtained by aligning the X-ray emitters 9 along a direction perpendicular to the forward movement direction 2 as illustrated for example in FIGS. 1, 5 and 6. FIG. 6, in particular, illustrates the result which may be obtained on the surface of the X-ray detecting device 10; the example shows four beams 11 of X-rays, whose incidence on the surface of the detecting device 10 is schematically illustrated (for each) by a rectangle with hatching angled to the right or to the left.

Figure 2:
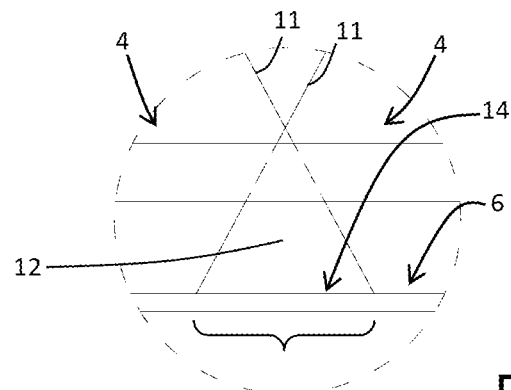
FIG. 2 is an enlarged view of the detail II of FIG. 1.
Figures 3, 4:
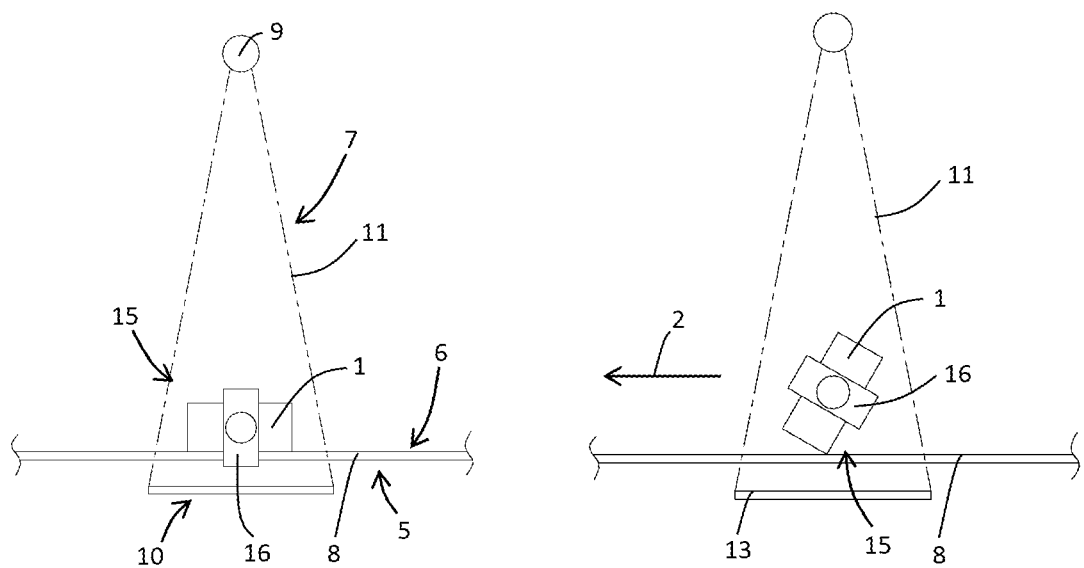
FIG. 3 is a schematic side view of the scanning zone of FIG. 1, in a first operating configuration.
FIG. 4 shows the scanning zone of FIG. 3, in a second operating configuration.

According to a particularly preferred embodiment, in order to guarantee that all of the axial portions 4 of the object 1 are affected by at least one beam 11 of X-rays, the X-ray emitters 9 are configured in such a way that the directions of irradiation of adjacent beams 11 of X-rays, extend in volumes which at least partly interfere with each other (hereinafter it shall be understood that reference is made to this interference between volumes defined by the irradiating directions even when, for simplicity, the text refers simply to interference between beams 11 of X-rays). In particular, as illustrated in FIGS. 1 and 2, in order to guarantee that the whole object 1 is subjected to the tomography inspection, it is preferably the case that the interference zone 12 between the volumes defined by the irradiating directions of the adjacent beams 11 of X-rays, starts at a height, relative to the forward movement plane 6, greater than the maximum thickness allowed for the objects 1 to be inspected. It should be noticed that when there is interference between two distinct beams 11 of X-rays, that occurs even at the detecting device 10. Below is an explanation of the problems which that may involve, and indications of the preferred solutions devised by the Applicant.

Figure 17:
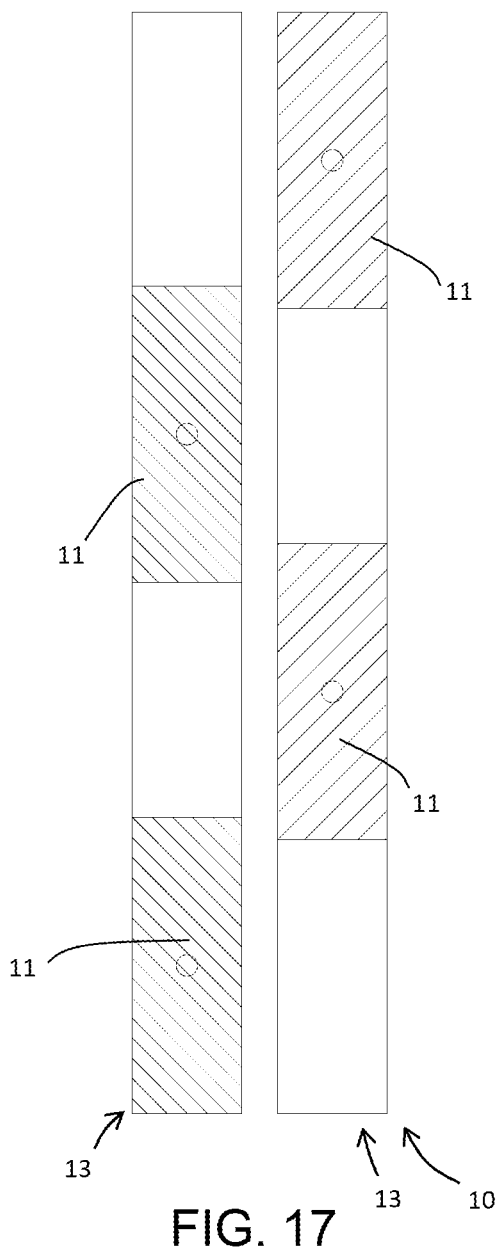
FIG. 17 is a schematic top view of the incidence of different beams of X-rays on two distinct sensors of a detecting device of an apparatus made according to a further embodiment of this invention.

In a different embodiment, in order to avoid overlapping zones of the type just described, the X-ray emitters 9 are instead grouped in two or more groups (FIG. 17 shows the case of only two groups).

In this case too the X-ray emitters 9 of each group are configured in such away that they emit respective beams 11 of X-rays which are aligned along a respective straight line transversal to the forward movement direction 2. What is different compared with the preceding case is that the straight lines for alignment of the various groups are spaced apart from each other along the forward movement direction 2, and that the X-ray emitters 9 are distributed in the two or more groups, in such a way that the axial portions 4 of the object 1 irradiated by the beams 11 of X-rays emitted by two adjacent emitters 9 of the same group, are separated by at least one portion also irradiated by a beam 11 of X-rays emitted by an X-ray emitter 9 of a different group. An example of this embodiment is illustrated in FIG. 17, where, similarly to what was described relative to FIG. 6, there is an illustration of the interference between the beams 11 of X-rays and the detecting device 10, this time constituted of to sensors side by side.

As in the case illustrated in FIG. 17, in the preferred embodiment the X-ray emitters 9 of each of the two groups are configured in such a way that the beams 11 of X-rays are overall positioned in a quincunx rows arrangement.

As regards the X-ray detecting device 10, similarly to the prior art devices, it is configured for generating, in use, radiographic data which represent, in electronic format, the intensity of the X-rays which strike it. In particular, it is configured for generating radiographic data which represent, in electronic format, the residual intensity of the X-rays emitted by the X-ray emitters 9 which reach the detecting device 10, in particular of those which reach it after having passed through an object 1 placed in the scanning zone 7.

In the preferred embodiments, the X-ray detecting device 10 comprises one or more two-dimensional sensors 13, which face towards the X-ray emitters 9, and advantageously are positioned in a plane perpendicular to a central axis of each beam 11 of X-rays which faces towards them. Each two-dimensional sensor 13 may be configured for receiving X-rays belonging to either a single beam 11 of X-rays or to a plurality of distinct beams 11 of X-rays. Each sensor 13 also advantageously comprises a two-dimensional matrix of detecting cells.

In particular, in a particularly preferred embodiment, each two-dimensional sensor 13 is configured for receiving X-rays belonging to a plurality of distinct beams 11 of X-rays, preferably those of all of the beams 11 of X-rays emitted by the X-ray emitters 9 of the same group.

If the adjacent beams 11 of X-rays overlap, on the surface of the detecting device 10 overlapping areas 14 can be identified, that is to say, areas of surface which are intersected by irradiating directions of X-rays belonging to two distinct beams 11 of X-rays (see in FIG. 6 the areas marked with cross-hatching).

As already referred to, those could create a problem in the reconstruction because the tomography reconstruction methods commonly used require the sensors 13 to each detect X-rays arriving from only one source.

However, since the X-rays are emitted with a divergent shape from emitters 9 which are almost punctiform, and since the objects 1 to be measured have a thickness that is not null, there are only two possible alternatives: either to leave zones of the object 1 which are not irradiated by any beam 11 of X-rays, or to accept that there are areas affected by two sources.

In the case of the first alternative, each two-dimensional sensor 13 configured for receiving X-rays belonging to a plurality of distinct beams 11 of X-rays, is advantageously positioned in such a way that on a detecting surface of it each area receives X-rays exclusively from one beam 11 of X-rays. However, in this case, the electronic processing and control unit will have to be programmed to process the tomography reconstruction of the object 1 by ignoring the parts of the object 1 through which beams 11 of X-rays do not pass. It should be noticed that the size of the parts of the object 1 through which no beams 11 of X-rays pass grows with an increase both in the inclination of the X-rays and in the thickness of the object 1.

However, in the preferred embodiments, the preference is for adoption of the second alternative indicated above, that is to say, to accept that there are areas potentially affected by two sources simultaneously, attempting to use other ways of overcoming the problems which this may cause for the tomography reconstruction.

According to a first embodiment, the apparatus comprises one or more shutters associated with each pair of beams 11 of X-rays to which an overlapping area 14 corresponds. As is known, shutters are electric or electromechanical devices, capable of very quickly blocking and reactivating the emission of X-rays. The shutters are synchronised with the detecting device 10 for selectively and alternately screening, at each detecting moment, one of the two beams 11 of X-rays, preventing them from reaching the overlapping area 14. Therefore, in this way it is possible to alternatively "activate" only one of the two beams 11 of X-rays, preventing the two emitters 9 from being able to simultaneously irradiate the same zone of the sensor 13. According to a second embodiment, in contrast use is made of collimators placed opposite the overlapping areas 14, suitable for screening the X-rays which arrive from directions other than a predetermined direction.

Therefore, the apparatus comprises a collimating unit associated with each overlapping area 14. In the context of this invention, the definition collimating unit preferably means a set of thin plates positioned in a way similar to anti-scatter grilles, made of a material capable of absorbing the X-rays arriving from directions other than the desired direction. At each detecting cell, the collimating unit is configured for selectively screening the X-rays of one of the two beams 11 and allowing the X-rays of the other beam to pass; in this way the X-rays of each of the two beams 11 of X-rays can selectively reach only one group of the detecting cells of each overlapping area 14. Preferably, the detecting cells of each group are also uniformly distributed in the overlapping area 14 itself. By acting in this way, at the overlapping zone a detecting resolution is obtained which is equal to half the resolution in the other zones of the detecting device 10. In order to distribute the detecting cells in the two groups as uniformly as possible, according to the preferred embodiments the distribution is in rows, with reference to the rows of detecting cells which in the overlapping zone extend perpendicularly to the forward movement direction 2; all of the detecting cells of one row are assigned to one group, all of the detecting cells of the two rows adjacent to the first, are assigned to the other group.

According to a further embodiment the electronic processing and control unit is programmed for processing the three-dimensional tomography reconstruction of the object 1, at least at the parts of the object 1 through which X-rays directed towards the overlapping areas 14 pass, using tomography reconstruction iterative algorithms.

An example of an algorithm of this type which could be used for this purpose is described in the Beister, Marcel, Daniel Kolditz, and Willi A. Kalender article. "*Iterative reconstruction methods in X-ray CT*" Physica medica 28.2 (2012): 94-108.

In all iterative methods it is assumed that there is a first reconstruction (for example based on the reconstructions obtainable for the adjacent axial portions 4 not affected by overlapping), ray-tracing is used to calculate the radiographic projections which should have been obtained if the object 1 were to actually correspond to the theoretical reconstruction, these projections are compared with the radiographic images measured, and the reconstruction is consequently corrected. By repeating this operation multiple times the algorithm converges on the correct solution.

In yet another embodiment, in contrast the reconstruction is performed using neural networks. Indeed, recently there has been positive testing of algorithms based on neural networks, wherein the network was trained to perform the tomography reconstruction in different situations (see for example Jin, Kyong Hwan, et al. "Deep convolutional neural network for inverse problems in imaging." IEEE Transactions on Image Processing 26.9 (2017): 4509-4522). In order to train a neural network of this type to perform the tomography reconstruction starting from data generated by multiple sources on the same sensor 13, it would be sufficient to simulate the projections from multiple sources starting from real scans or known tomography reconstructions, and to teach the network to perform the tomography inversion.

Finally, it should be noticed that, on the whole, the one or more sensors 13 of the detecting device 10 must have a very large surface, since they must substantially cover the whole object 1 during the rotation. This could involve very high costs if single or panel-type sensors 13 were used. A preferred and less expensive solution, explained in detail in European patent application No. 19155347 by this same Applicant (the content of which should be referred to for further details), involves using as sensors 13, thin scintillator sheets, which convert the X-rays into visible light photons, and then framing those scintillator sheets with an array of low cost video cameras.

Moreover, according to a further aspect of this invention, in order to allow the acquisition of radiographic data about the object 1 from different angles, the apparatus also comprises at least one rotation device 15 for rotating the objects 1 which is associated with the scanning zone 7.

The rotation device 15 is configured for rotating each object 1 on itself about its own main axis of extension 3, preferably by at least 180°, whilst the object 1 itself is irradiated by one or more beams 11 of X-rays. In particular, if the objects 1 are wooden boards, advantageously the rotation device 15 causes the board to overturn on the forward movement plane 6 (FIGS. 7-11 and 12-16).

In particular in the embodiments where higher productivity is required, preferably the rotation device 15 causes a rotation of the object 1 on itself which is at least partly uncontrolled and/or it does this without interrupting the forward movement of the objects 1.

Depending on requirements, the rotation device 15 may therefore be made in different ways.

In a first embodiment illustrated in FIG. 1, the rotation device 15 comprises at least one mechanical unit 16 which is switchable between an operating configuration in which in use it can retain an end of the object 1 (for example a gripper), and a home configuration in which in use it does not engage with the end of the object 1. The mechanical unit 16 is also configured for rotating the object 1 by acting on the end of the object 1 retained by it in the operating configuration. Depending on the cases, a single mechanical unit 16 at one of the ends of the object 1 may be used, leaving the object 1 partly resting on the conveyor 5, or there may be two mechanical units 16 which each act at one end of the object 1, also lifting the object off the conveyor 5 in order to make it rotate.

There are also embodiments in which the mechanical unit 16 is stationary relative to the forward movement direction 2 and can only rotate on itself if necessary raising or lowering itself relative to the forward movement plane 6, and embodiments in which the mechanical unit 16 is movable along the forward movement direction 2 and, whilst it rotates the object 1, follows the movement of the object along the forward movement direction 2.

According to an embodiment which provides for an uncontrolled rotation of the object 1, the rotation device 15 comprises pushing means 17 for the object 1 which are associated with the conveyor 5 for pushing the object 1 on the forward movement plane 6 along the forward movement direction 2, and one or more fixed obstacles 18 which are mounted along the forward movement direction 2 transversally to it.

The fixed obstacles 18, in use, intercept the object 1 during its movement on the forward movement plane 6, and temporarily block its longitudinal forward movement. At the same time, the fixed obstacles 18 allow the rotation of the object 1 about them, following the action applied by the pushing means 17 which continue moving forward with the conveyor 5. In more detail, the pushing means 17 (which, like the fixed obstacles 18 must be suitably shaped) may gradually cause the rear part of the object 1 to lift up, rotating it about a variable centre of instantaneous rotation, defined by the interaction between the front part of the object 1 and the fixed obstacles 18, as is schematically illustrated in FIGS. 7 to 11.

In contrast, in another particularly preferred embodiment, the rotation of the object 1 is obtained by striking the object 1 at a zone of it which is off-centre relative to the barycentre and making it perform a sort of half "somersault", forward, or backward, on the conveyor 5. Rotation devices of this type are in themselves known and already widely used for other purposes in wooden board processing plants; therefore they will not be described in detail herein.

However, in general, a rotation device 15 of this type comprises one or more percussion units 19 which are mounted below the forward movement plane 6, and which are movable between a home position, in which they are positioned completely below the forward movement plane 6, and an operating position, in which they at least partly project upward relative to the forward movement plane 6. The movement between the two positions may occur in any way, for example by means of rotation (as in the case illustrated in the accompanying figures), or by means of straight line translation of the whole percussion unit or only a part of it. Associated with the percussion units 19 there are movement means (not illustrated), which are configured for moving them between the home position and the operating position. The movement means and the percussion units 19 are synchronised with the conveyor 5 in such a way that, in use, the percussion units 19 are moved (all together) from the home position to the operating position for striking (practically simultaneously) an off-centre zone (front or rear) of the object 1 placed in the scanning zone 7. The synchronisation with the conveyor 5 may be obtained either by constantly monitoring the position of the objects 1 or by using specific sensors 13. Everything is also sized in such a way that the percussion units 19 strike the object 1 with an amount of motion such that it causes rotation of the object 1 about its own axis of rotation as illustrated for example in FIGS. 12 to 16.

If the beams 11 of X-rays are not all aligned along the same straight line, advantageously the apparatus comprises a rotation device 15 for rotating the objects 1 at each group of X-ray emitters 9 (or each position along the forward movement direction 2, at which one or more beams 11 of X-rays are present). Finally, it should be noticed that in all of the cases just described, during rotation of each object 1, the rotation device 15 also inevitably causes bending of the object 1 relative to the main axis of extension 3, even though this is unwanted bending. This is particularly significant in the case of wooden boards which are several metres long.

A further feature of the apparatus according to this invention is the presence of electronic identifying means, which are configured for estimating the instantaneous position and orientation of the axial portions 4 of an object 1 at least while those axial portions 4 are irradiated by one of the beams 11 of X-rays. Various examples of electronic means usable for that purpose are described in patent application Ser. No. 10/201,9000019454 by this same Applicant, the content of which should be referred to for further details.

Therefore, the electronic identifying means are active at least at the scanning zone 7 and, depending on requirements may be configured for estimating the position and the orientation of a single axial portion 4 of the object 1 (it then being possible to infer the positions and the orientation of the other axial portions 4 from that of the axial portion 4 for which the estimate was effectively made) for example altogether estimating the position and the orientation of the object 1 as a whole, or may be configured for estimating the position and the orientation of a plurality of distinct axial portions 4.

As already indicated, the electronic identifying means in general "estimate" the position and the orientation of the axial portion 4 meaning that they perform a measurement of these with a predetermined degree of precision, which may be more or less high depending on the ways of measuring adopted and the level of precision required for the tomography reconstruction.

Therefore, the need to perform that measurement for a more or less large number of axial portions 4, mainly depends on the type of rotation device 15 used and on the flexibility of the object 1 being inspected. Indeed, the greater the bending deformation which may affect the object 1 during the rotation is, the greater the usefulness of estimating the position and the orientation of distinct axial portions 4 is. In contrast, if the object 1 could be considered substantially rigid, that is to say, such that it is not subject to perceptible deformations during the rotation, then estimating the position and the orientation of a single axial portion 4 would be sufficient to estimate with just as much precision the position and the orientation of all of the other axial portions 4.

In a first embodiment, wherein the rotation device 15 is constituted of a mechanical unit 16, the electronic identifying means may comprise a control unit for controlling operation of the rotation device 15, also programmed to determine the position and/or the orientation of the objects 1 based on the position and/or the orientation of the mechanical unit 16.

In contrast, in other embodiments, the electronic identifying means are configured for estimating the position and/or the orientation by observing the axial portion 4 of interest.

In a first embodiment, for example, the electronic identifying means may comprise one or more video cameras 20, configured for framing each axial portion 4 of interest while it remains in the scanning zone 7, and a processing unit, connected to the one or more video cameras 20 for receiving the images acquired by them, and programmed for processing the images and for determining the position and/or the orientation of the axial portions 4 at the moments of interest by comparing the images with each other; advantageously the image of the object 1 while it is on the forward movement plane 6 may be used as a reference image, and all of the other positions may be defined relative to it (even if other methods may also be used). In place of traditional video cameras 20 depth video cameras 20 may also be used.

In contrast, in a different embodiment, the electronic identifying means comprise one or more laser detecting devices for detecting the surface shape of the axial portions 4 of interest, and a processing unit, connected to the one or more laser detecting devices, for receiving from them the data relating to the shape and the position of the surface of the object 1, and programmed for processing that data in order to determine the position and/or the orientation of the axial portions 4 at the moments of interest.

In a variant even combined solutions may be used which comprise both one or more video cameras 20, and one or more laser devices.

In contrast, in a different embodiment, the electronic identifying means are constituted of the electronic processing and control unit which is programmed for determining the position and/or the orientation of each axial portion 4 of interest, processing the radiographic data relative to that axial portion 4 which are acquired at the moment of interest by the detecting device 10. This is particularly advantageous in the case in which the dimensions of the object 1, and/or its density distribution, are known beforehand, for example thanks to previous inspections performed on the object 1 itself (as often occurs, for example, for wooden boards).

According to a further feature of this invention, the electronic processing and control unit is connected at least to the X-ray emitters 9, to the X-ray detecting device 10 and to the electronic identifying means.

In particular, the electronic processing and control unit is connected to the X-ray emitters 9 for controlling their activation, for example either switching them between a switched on configuration and a switched off configuration, or controlling any systems for interrupting the beams 11 of X-rays associated with them, such as the shutters described above.

The electronic processing and control unit is connected to the X-ray detecting device 10 for receiving from it the radiographic data generated by it, either continuously (that is to say, with the updating frequency allowed by the X-ray detecting device 10) or intermittently (that is to say, only at moments of interest, whether predetermined or not).

The electronic processing and control unit is in contrast connected to the electronic identifying means, for receiving from them information about the position and the orientation of each axial portion 4 of the object 1, relative to the beam 11 of X-rays which strikes it at the moments of interest.

The electronic processing and control unit is also programmed for repeatedly performing several operations while the object 1 remains in the scanning zone 7, and in particular, at least at each of a plurality of distinct detecting moments, at which the object 1 has a different position and/or a different orientation. Indeed, for each axial portion 4 irradiated by a beam 11 of X-rays, the electronic processing and control unit is programmed to acquire a set of radiographic data from the detecting device 10, and corresponding information about the position and the orientation from the electronic identifying means, at each detecting moment.

It should be noticed that the detecting moments may be the same for all of the axial portions 4 (for example in the case in which all of the beams 11 of X-rays are aligned along a single straight line transversal to the forward movement direction 2 and in which collimators are used for managing the overlapping areas 14) or may be completely or partly different for the different axial portions 4 (for example in the case in which the beams 11 of X-rays are generated with a quincunx rows arrangement with the need to perform a double rotation of the object 1 about the main axis of extension 3, or in the case in which shutters are used for managing the overlapping problems).

Advantageously, it is appropriate that for each axial portion 4 a number of different sets of radiographic data is available, which is equal to or greater than the minimum number of radiographic images necessary for a tomography reconstruction with the desired precision. It is also appropriate for such sets of radiographic data to be acquired from angles which are distributed about the main axis of extension 3 in a sufficiently uniform way. For that purpose, the detecting moments are advantageously concentrated in the time interval during which the rotation of the object 1 on itself occurs, and are preferably uniformly distributed in it.

Finally, the electronic processing and control unit is programmed for combining the sets of radiographic data acquired, for each axial portion 4 of the object 1, at the relative different detecting moments, and on the basis of the corresponding information about the position and the orientation, for processing a three-dimensional tomography reconstruction of the object 1.

Depending on the embodiments, the electronic processing and control unit may be constituted of a single computer or of multiple distinct computers which are connected to each other.

It should also be noticed that both the conveyor 5 (the part which supports the object 1 and moves it forward) and the rotation device 15 are also in the scanning zone 7. If these are made of material which absorbs the X-rays a lot, zones in which the measurement signal is too attenuated could be created. One solution for overcoming this problem is to use materials which are not very absorbent, such as plastic or carbon fibre. A further solution is to use a support for the conveyor chains which is of the type described in patent application EP 3220143 A1 (to which reference should be made for further details), provided that the X-ray emitters 9 are positioned below the forward movement plane 6 and the detecting device 10 above it.

As already indicated above, the various embodiments of the apparatus described so far are capable of implementing the method according to this invention, at least in its most general embodiment.

That method comprises first making the object 1 move forward along a forward movement direction 2 perpendicular to the main axis of extension 3, making it pass through at least one scanning zone 7.

In the at least one scanning zone 7, the method comprises irradiating the object 1 with a plurality of beams 11 of X-rays, each generated by a different fixed X-ray emitter 9, and for each beam 11 of X-rays to be generated in such a way as to irradiate an axial portion 4 of the object 1 which is at least partly distinct from those irradiated by the other beams 11 of X-rays. Advantageously, the steps of irradiating the object 1 is performed using divergent beams 11 of X-rays, and the beams 11 of X-rays are generated in such a way that they irradiate the whole volume of the object 1 (therefore with overlapping).

While each axial portion 4 of interest is irradiated by the respective beam 11 of X-rays, the method comprises rotating that axial portion 4 (that is to say, the whole object 1) about the main axis of extension 3, preferably by at least 180°, using a device of the mechanical type, such as those described above relative to the apparatus, or others of a different type. Preferably, the step of rotating each axial portion 4 is performed by making the whole object 1 rotate on itself in a way that is at least partly uncontrolled.

At a plurality of distinct positions and/or orientations adopted by each axial portion 4 relative to the respective beam 11 of X-rays which irradiates it (in particular at a plurality of different detecting moments during the rotation) the method comprises detecting respective sets of radiographic data, which represent the residual intensity at least of the X-rays which have passed through that axial portion 4 at each detecting moment. In particular, the method comprises the acquisition occurring using a fixed detecting device 10, facing the x-ray emitters 9.

Furthermore, the method comprises generating information about the position and the orientation of each axial portion 4, relative to the respective beam 11 of X-rays which irradiates it, at each detecting moment, advantageously using electronic identifying means.

Finally, using the sets of radiographic data detected in this way and the corresponding information about the position and the orientation of each axial portion 4 at the moment of acquisition of the sets of radiographic data, the method comprises performing a three-dimensional tomography reconstruction of the object 1.

In one embodiment, the method also requires the step of irradiating the object 1 with a plurality of beams 11 of X-rays to be performed twice, at two distinct parts of the scanning zone 7. In particular it requires that each time, only one group of axial portions 4, which are distinct and axially spaced from each other, is irradiated by the respective beam 11 of X-rays. Moreover, the axial portions 4 irradiated the first time are different from those irradiated the second time, so that the whole of each axial portion 4 is irradiated only once (situation illustrated for example in FIG. 17). Finally, the step of rotating each axial portion 4 about the main axis of extension 3 is implemented at least once at each of the distinct parts of the scanning zone 7.

Alternatively, the method may require the steps of irradiating the object 1 with a plurality of beams 11 of X-rays, and of rotating each axial portion 4, to be performed only once simultaneously for all of the axial portions 4.

This invention brings important advantages.

In particular, thanks to this invention it has been possible to define an apparatus and a method for performing a computed tomography scan of objects which have an elongate shape, which with a cost comparable to that of the prior art apparatuses, allow complete tomography scans to be performed of large objects 1, such as wooden boards, with the productivity levels required by the plants currently used.

Finally, it should be noticed that this invention is relatively easy to produce and that even the cost linked to implementing the invention is not very high.

The invention described above may be modified and adapted in several ways without thereby departing from the scope of the inventive concept.

All details may be substituted with other technically equivalent elements and the materials used, as well as the shapes and dimensions of the various components, may vary according to requirements.

The invention claimed is:

1. Apparatus for performing computed tomography scans of objects (1) which have an elongate shape, wherein each object (1) has a main axis of extension (3) along which a plurality of axial portions (4) of the object (1) itself are identifiable, the apparatus comprising:
    a conveyor (5) configured for conveying, along a forward movement direction (2), objects (1) which are positioned on a forward movement plane (6) with the main axis of extension (3) transversal to the forward movement direction (2), from an infeed zone to an outfeed zone and through at least one scanning zone (7);
    a plurality of X-ray emitters (9) which are facing the conveyor (5) at the at least one scanning zone (7), for in use emitting respective beams (11) of X-rays towards each object (1) which passes through the scanning zone (7), the beam (11) of X-rays emitted by each X-ray emitter (9) being offset, with reference to the forward movement direction (2), relative to the beams (11) of X-rays emitted by the other X-ray emitters (9), in such a way that each beam (11) of X-rays irradiates an axial portion (4) of each object (1) which is at least partly distinct from the axial portions (4) irradiated by the other beams (11) of X-rays;
    an X-ray detecting device (10) facing the X-ray emitters (9) for, in use, generating radiographic data which represent, in electronic format, the residual intensity of the X-rays emitted by the X-ray emitters (9) and which have passed through an object (1) placed in the scanning zone (7), where the X-ray emitters (9) and the X-ray detecting device (10) are stationary relative to the conveyor (5) and are positioned on opposite sides of the forward movement plane (6) defined by the conveyor (5);
    at least one rotation device (15) for rotating the objects (1), associated with the scanning zone (7), and configured for rotating each object (1) on itself about its own main axis of extension (3), while the object (1) is irradiated by one or more of said beams (11) of X-rays;
    electronic identifying means for estimating the instantaneous position and orientation of the axial portions (4) of an object (1) which are irradiated by one of said beams (11) of X-rays; and
    an electronic processing and control unit;
    wherein the electronic processing and control unit is connected to the X-ray emitters (9) for controlling their activation, to the X-ray detecting device (10) for receiving the radiographic data generated by it, and to the electronic identifying means for receiving from them information about the position and the orientation of each axial portion (4) of the object (1) relative to the beam (11) of X-rays which strikes it;
    wherein, while the object (1) remains in the scanning zone (7) and at least at each of a plurality of distinct detecting moments at which the object (1) has a different position and/or a different orientation, for each beam (11) of X-rays and the corresponding axial portion (4) of the object irradiated by it, the electronic processing and control unit is programmed to acquire a corresponding set of radiographic data from the detecting device (10) and corresponding information about the position and the orientation of the axial portion (4) from the electronic identifying means;
    and wherein the electronic processing and control unit is programmed for combining the sets of radiographic data acquired for each axial portion (4) of the object (1) at the different detecting moments, on the basis of the corresponding information about the position and the orientation, for processing a three-dimensional tomography reconstruction of the object (1).

2. Apparatus according to claim 1 wherein the X-ray emitters (9) are grouped in a single group and are configured in such a way that they emit respective beams (11) of X-rays which are side by side one after another in a direction transversal to the forward movement direction (2).

3. Apparatus according to claim 2 wherein the X-ray emitters (9) emit respective divergent beams (11) of X-rays and are configured in such a way that adjacent beams (11) of X-rays at least partly interfere with each other at least at the detecting device (10).

4. Apparatus according to claim 1 wherein the X-ray emitters (9) are grouped in two or more groups, and wherein the X-ray emitters (9) of each group are configured in such a way that they emit respective beams (11) of X-rays which are aligned along a straight line which is transversal to the forward movement direction (2) and is spaced along the forward movement direction (2) from the straight line along which the beams (11) of the other group are aligned.

5. Apparatus according to claim 4, wherein the X-ray emitters (9) of each group are configured in such a way that the beams (11) of X-rays are overall positioned with a quincunx rows arrangement.

6. Apparatus according to claim 4 comprising a rotation device (15) for rotating the objects (1) at each group of X-ray emitters (9).

7. Apparatus according to claim 1 wherein the X-ray detecting device (10) comprises either one or more two-dimensional sensors (13) which are facing towards the X-ray emitters (9), and wherein each two-dimensional sensor (13) is configured for receiving X-rays belonging either to a single beam (11) of X-rays or to a plurality of distinct beams (11) of X-rays.

8. Apparatus according to claim 7 wherein each two-dimensional sensor (13) is configured for receiving X-rays belonging to a plurality of distinct beams (11) of X-rays, and is positioned in such a way that on a detecting surface thereof it is possible to identify overlapping areas (14) intersected by irradiating directions of X-rays belonging to two distinct beams (11) of X-rays.

9. Apparatus according to claim 8 also comprising one or more shutters associated with each pair of beams (11) of X-rays to which an overlapping area (14) corresponds, and wherein the shutters are synchronised with the detecting device (10) for selectively and alternately screening, at each detecting moment, one of the two beams (11) of X-rays, preventing them from reaching the overlapping area (14).

10. Apparatus according to claim 8 wherein in each overlapping area (14) the detecting device (10) comprises a two-dimensional matrix of detecting cells, wherein the apparatus also comprises a collimating unit associated with each overlapping area (14), and wherein, at each detecting cell, the collimating unit is configured for selectively screening the X-rays of one of the two beams (11) and allowing the X-rays of the other beam to pass, in such a way that the X-rays of each of the two beams (11) of X-rays can selectively reach only one group of the detecting cells of each overlapping area (14), where the detecting cells of each group are uniformly distributed in the overlapping area (14) itself.

11. Apparatus according to claim 8 wherein the electronic processing and control unit is programmed either not to process the tomography reconstruction for parts of the object (1) through which X-rays directed towards the overlapping areas (14) pass, or to process the three-dimensional tomography reconstruction of the object (1), at least at the parts of the object (1) through which X-rays directed towards the overlapping areas (14) pass, using tomography reconstruction iterative algorithms or neural networks trained for that purpose.

12. Apparatus according to claim 7 wherein each two-dimensional sensor (13) is configured for receiving X-rays belonging to a plurality of distinct beams (11) of X-rays, and is positioned in such a way that on a detecting surface thereof each area receives X-rays exclusively from one beam (11) of X-rays, and wherein the electronic processing and control unit is programmed for processing the tomography reconstruction of the object (1) by ignoring parts of the object (1) through which beams (11) of X-rays do not pass.

13. Apparatus according to claim 1 wherein the rotation device (15) comprises at least one mechanical unit (16) which is switchable between an operating configuration in which in use it can retain an end of the object (1) and a home configuration in which in use it does not engage with the end of the object (1), and which is configured for rotating the object (1) by acting on that end of the object retained by it in the operating configuration.

14. Apparatus according to claim 13 wherein the mechanical unit (16) is stationary relative to the forward movement direction (2) or movable along the forward movement direction (2).

15. Apparatus according to claim 13 wherein the electronic identifying means comprise a control unit for controlling operation of the rotation device (15) programmed to determine the position and/or the orientation of the objects (1) or of one or more of their axial portions (4) based on the position and/or the orientation of the mechanical unit (16).

16. Apparatus according to claim 13 wherein, during rotation of each object (1), the rotation device (15) also causes bending of the object (1) relative to the main axis of extension (3).

17. Apparatus according to claim 1 wherein the rotation device (15) comprises pushing means (17) for pushing the object (1) which are associated with the conveyor (5) for pushing the object (1) on the forward movement plane (6) along the forward movement direction (2) and one or more fixed obstacles (18) which in use intercept the object (1) during its movement on the forward movement plane (6) for temporarily blocking its longitudinal forward movement and allowing it to rotate about the one or more obstacles following the action applied by the pushing means (17).

18. Apparatus according to claim 1 wherein the rotation device (15) comprises one or more percussion units (19) which are mounted below the forward movement plane (6), and which are movable between a home position, in which they are positioned completely below the forward movement plane (6), and an operating position, in which they at least partly project upward relative to the forward movement plane (6), and movement means for the percussion units (19), the movement means and the percussion units (19) being configured and synchronised with the conveyor (5) in such a way that, in use, the percussion units (19) are moved from the home position to the operating position for striking an off-centre zone of the object (1) placed in the scanning zone (7) with an amount of motion such that it causes rotation of the object (1) about its own axis of rotation.

19. Apparatus according to claim 1 wherein the rotation device (15) causes a rotation of the object (1) on itself which is at least partly uncontrolled.

20. Apparatus according to claim 1 wherein the electronic identifying means comprise:
one or more video cameras (20) configured for framing each object (1) while it remains in the scanning zone (7), and a processing unit connected to the one or more video cameras (20) for receiving the images acquired by them, and programmed for processing the images for determining the position and/or the orientation of the object (1) or of its axial portions (4) at the detecting moments; and/or one or more laser detecting devices for detecting the surface shape of the objects (1), and a processing unit connected to the one or more laser detecting devices for receiving from them the data relating to the shape and the position of the surface of the object (1), and programmed for processing that data in order to determine the position and/or the orientation of the object (1) or of its axial portions (4) at the detecting moments.

21. Apparatus according to claim 1 wherein the electronic identifying means are constituted of the electronic processing and control unit which is programmed to determine the position and/or the orientation of the objects (1) or of their axial portions (4) by processing the sets of radiographic data relative to each detecting moment.

22. Apparatus according to claim 1 wherein the electronic identifying means estimate the instantaneous position and orientation of each axial portion (4) of the object (1), estimating an instantaneous position and orientation of the object (1) as a whole.

23. Method for performing a computed tomography scan of an object (1) which has an elongate shape along a main axis of extension (3) along which a plurality of axial portions (4) of the object (1) itself are identifiable, the method comprising the operating steps of:

making the object (1) move forward along a forward movement direction (2) perpendicular to the main axis of extension (3), through at least one scanning zone (7);

in the at least one scanning zone (7) irradiating the object (1) with a plurality of beams (11) of X-rays which are each generated by a different fixed X-ray emitter (9), each beam (11) of X-rays irradiating an axial portion (4) of the object (1) which is at least partly distinct from those irradiated by the other beams (11) of X-rays;

while each axial portion (4) is irradiated by the respective beam (11) of X-rays, using a mechanical device to rotate that axial portion (4) about the main axis of extension (3);

for a plurality of distinct positions and/or orientations adopted at a plurality of different detecting moments, by each axial portion (4) relative to the respective beam (11) of X-rays which irradiates it, using a fixed detecting device (10) which is facing the X-ray emitters (9), detecting respective sets of radiographic data which represent the residual intensity of the X-rays which have passed through that axial portion (4) at each detecting moment;

using electronic identifying means, generating information about the position and the orientation of each axial portion (4) relative to the respective beam (11) of X-rays which irradiates it at each detecting moment; and using the sets of radiographic data detected in this way and the corresponding information about the position and the orientation of each axial portion (4) at the moment of acquisition of the sets of radiographic data, performing a three-dimensional tomography reconstruction of the object (1).

24. Method according to claim 23 wherein the step of irradiating the object (1) with a plurality of beams (11) of X-rays is performed twice at two distinct parts of the scanning zone (7), each time only one group of axial portions (4) which are distinct and axially spaced from each other being irradiated by the respective beam (11) of X-rays, and the axial portions (4) irradiated the first time being different from those irradiated the second time, and wherein the step of rotating each axial portion (4) about the main axis of extension (3) is implemented at least once at each of said distinct parts of the scanning zone (7).

25. Method according to claim 23 wherein the step of irradiating the object (1) with a plurality of beams (11) of X-rays and of rotating each axial portion (4) are performed only once simultaneously for all of the axial portions (4).

26. Method according to claim 25 wherein the step of irradiating the object (1) is performed using divergent beams (11) of X-rays and wherein the beams (11) of X-rays are generated in such a way that they irradiate the whole volume of the object (1).

27. Method according to claim 23 wherein the step of rotating each axial portion (4) is performed by making the whole object (1) rotate on itself in a way that is at least partly uncontrolled.

\* \* \* \* \*